United States Patent
Cooke et al.

(10) Patent No.: US 6,469,227 B1
(45) Date of Patent: Oct. 22, 2002

(54) ANTIPRURITIC PATCH

(75) Inventors: Dede Cooke, Wayzata; David Rolf, Eden Prairie, both of MN (US)

(73) Assignee: LecTec Corporation, Minnetonka, MN (US)

( * ) Notice: Subject to any disclaimer, the term of this patent is extended or adjusted under 35 U.S.C. 154(b) by 0 days.

(21) Appl. No.: 09/569,783

(22) Filed: May 12, 2000

Related U.S. Application Data

(60) Provisional application No. 60/170,041, filed on Dec. 10, 1999.

(51) Int. Cl.[7] .......................... A61F 13/00; A61F 13/02; A61L 15/00; A61L 15/16
(52) U.S. Cl. .......................... 602/48; 602/54; 424/443; 424/445; 424/447; 424/448; 604/304; 604/307
(58) Field of Search ...................... 602/41–59; 604/304, 604/305, 306, 307; 442/441–448; 128/888, 889, 893, 894

(56) References Cited

U.S. PATENT DOCUMENTS

| | | | |
|---|---|---|---|
| 2,137,169 A | 11/1938 | Leven | 167/84 |
| 3,249,109 A | 5/1966 | Maeth et al. | |
| 3,339,546 A | 9/1967 | Chen | |
| 3,428,043 A | 2/1969 | Shepherd | |
| 3,598,122 A | 8/1971 | Zaffaroni | |
| 3,612,053 A | 10/1971 | Pratt | |
| 3,640,741 A | 2/1972 | Estes | 106/170 |
| 3,731,683 A | 5/1973 | Zaffaroni | |
| 3,742,951 A | 7/1973 | Zaffaroni | |
| 3,767,784 A | 10/1973 | Gluck | 424/28 |
| 3,814,095 A | 6/1974 | Lubens | 128/260 |
| 3,972,995 A | 8/1976 | Tsak et al. | 424/28 |
| 3,998,215 A | 12/1976 | Anderson et al. | 128/2.06 E |
| 4,002,221 A | 1/1977 | Buchalter | 181/0.5 |
| 4,089,329 A | 5/1978 | Couvillon, Jr. et al. | 128/2 T |
| 4,125,110 A | 11/1978 | Hymes | |
| 4,243,656 A | 1/1981 | Walliczek | 424/28 |
| 4,253,460 A | 3/1981 | Chen et al. | |
| 4,274,420 A | 6/1981 | Hymes | |
| 4,299,231 A | 11/1981 | Karmann et al. | |
| 4,306,551 A | 12/1981 | Hymes et al. | |
| 4,307,717 A | 12/1981 | Hymes et al. | |
| 4,452,892 A | 6/1984 | Rosevear | 435/176 |
| 4,457,748 A | 7/1984 | Lattin et al. | 604/20 |
| 4,474,570 A | 10/1984 | Ariura et al. | 604/20 |
| 4,515,162 A | 5/1985 | Yamamoto et al. | |

(List continued on next page.)

FOREIGN PATENT DOCUMENTS

| | | | |
|---|---|---|---|
| EP | 0 072 251 | 2/1983 | |
| EP | 0156565 | 10/1985 | A61L/15/03 |

OTHER PUBLICATIONS

"Co–pending Appliaton SN 08/054,745, filed Apr. 26, 1993: Solid Multipurpose Ultrasonic Biomedical Couplaant Gel In Sheet Form and Method."

"External Analgesic Drug Products for Over–the Counter Use; Tentative Final Momograph", *Federal Register*, 19 pages, (Feb. 8, 1983).

*Primary Examiner*—Kim M. Lewis
(74) *Attorney, Agent, or Firm*—Schwegman, Lundberg, Woessner & Kluth, P.A.

(57) ABSTRACT

The present invention provides a non-occlusive adhesive skin patch. The patch includes a woven or nonwoven porous backing having a front side and a back side. The patch also includes a therapeutic formulation located on the front side of the backing. The backing includes a flexible sheet of water insoluble porous material. The therapeutic formulation includes a medicament useful for relieving topical discomfort and a pressure sensitive adhesive. The therapeutic formulation optionally includes a solvent that can effectively dissolve the medicament. The present invention also provides a method for alleviating topical discomfort. The method includes applying an adhesive skin patch of the present invention to skin inflicted with a topical disorder.

46 Claims, 4 Drawing Sheets

U.S. PATENT DOCUMENTS

| | | | |
|---|---|---|---|
| 4,585,652 A | 4/1986 | Miller et al. .................. 424/83 |
| 4,593,053 A | 6/1986 | Jevne et al. ................. 523/111 |
| 4,638,043 A | 1/1987 | Szycher et al. ............... 528/75 |
| 4,668,564 A | 5/1987 | Orchard ...................... 428/246 |
| 4,675,009 A | 6/1987 | Hymes et al. .............. 604/304 |
| 4,692,273 A | 9/1987 | Lawrence ................... 252/518 |
| 4,694,835 A | 9/1987 | Strand |
| 4,696,854 A | 9/1987 | Ethier ........................ 428/287 |
| 4,702,732 A | 10/1987 | Powers et al. ................ 604/20 |
| 4,704,282 A | 11/1987 | Campbell et al. ........... 424/449 |
| 4,717,378 A | 1/1988 | Perrault et al. ............... 604/20 |
| 4,725,439 A | 2/1988 | Campbell et al. ........... 424/449 |
| 4,778,786 A | 10/1988 | Reever et al. ................ 514/54 |
| 4,803,078 A | 2/1989 | Sakai ......................... 424/445 |
| 4,867,982 A | 9/1989 | Campbell et al. ........... 424/449 |
| 4,989,607 A | 2/1991 | Keusch et al. |
| 5,002,792 A | 3/1991 | Vegoe ............................ 472/2 |
| 5,024,838 A * | 6/1991 | Parrilla ....................... 424/443 |
| 5,120,544 A | 6/1992 | Henley ....................... 424/443 |
| 5,123,423 A | 6/1992 | Scharnberg |
| 5,124,157 A | 6/1992 | Colley et al. ............... 424/448 |
| 5,142,817 A | 9/1992 | Rolf .............................. 47/24 |
| 5,175,052 A | 12/1992 | Tokuda et al. ........ 428/355 AC |
| 5,205,297 A | 4/1993 | Montecalvo et al. |
| 5,224,967 A | 7/1993 | Rolf et al. ..................... 47/58 |
| 5,423,737 A | 6/1995 | Cartmell et al. .............. 602/57 |
| 5,501,661 A | 3/1996 | Cartmell et al. .............. 602/58 |
| 5,522,878 A | 6/1996 | Montecalvo et al. ....... 607/152 |
| 5,536,263 A | 7/1996 | Rolf et al. ................... 604/307 |
| 5,589,192 A | 12/1996 | Okabe et al. ............... 424/486 |
| 5,741,510 A | 4/1998 | Rolf et al. ................... 424/448 |

\* cited by examiner

ANTIPRURITIC PATCH

RELATED APPLICATION

The present application claims priority under 35 U.S.C. 119 to U.S. Provisional Application Ser. No. 60/170,041, filed 10 Dec. 1999; which application is incorporated herein by reference.

BACKGROUND OF THE INVENTION

Several patch devices have been used for applying medication to the skin. For example, U.S. Pat. Nos. 4,675,009; 5,536,263; and 5,741,510 each describe a drug dispensing device for the delivery of medication to the skin. While the patches disclosed are generally effective in the delivery of a medicament (e.g., antipruritic) to the skin, there exists a need for additional protective, adhesive patches that can adhere to FDA regulations.

FDA regulations (e.g., Federal Register, Vol. 48, No. 27, §341) regulate what components (i.e., "active ingredients"), in a specified amount, may be described as relieving itching (i.e., contains a topical antipruritic). In order to follow FDA regulations, therefore, only a select number of active ingredients that are able to relieve itching, in a specified amount, may be included in an adhesive patch when the patch is described as a relieving itching. Consequently, it is difficult to manufacture a vapor permeable adhesive patch that includes a topical antipruritic, while at the same time maintaining (a) the solubility and stability of the active ingredients in the therapeutic formulation, (b) the pressure sensitive adhesive properties of the therapeutic formulation, and (c) following FDA regulations.

Accordingly, there is a need for a protective adhesive patch that can be topically applied, that can relieve topical discomfort, that can prevent the user from touching the topical discomfort, and that can cover the entire area of the skin inflicted with the topical disorder. Preferably, the patch is vapor permeable (i.e., breathable).

The patch should be able to maintain the solubility and stability of the medicament (e.g., topical antipruritic) during the manufacturing, packaging, shipping, and/or storage of the patch, while maintaining the pressure sensitive adhesive properties of the therapeutic formulation. In addition, the patch should adhere to FDA regulations (e.g., Federal Register, Vol. 48, No. 27, §348).

SUMMARY OF THE INVENTION

The present invention provides an adhesive patch. The adhesive patch includes a backing of a flexible sheet of water insoluble porous material. The backing has a front side and a back side and a therapeutic formulation positioned on at least a portion of the front side of the backing. The therapeutic formulation includes a medicament useful for relieving topical discomfort and a pressure sensitive adhesive.

The invention also provides a second adhesive patch. The second adhesive patch includes a backing of a flexible sheet of water insoluble porous material. The backing has a front side and a back side and a therapeutic formulation positioned on at least a portion of the front side of the backing. The therapeutic formulation includes a medicament useful for relieving topical discomfort and a pressure sensitive adhesive. The second adhesive patch can effectively cover the entire surface of skin inflicted with the topical disorder.

The invention also provides a third adhesive patch. The third adhesive patch includes a backing of a flexible sheet of water insoluble porous material. The backing has a front side and a back side and an ointment positioned on at least a portion of the front side of the backing. The ointment includes a medicament useful for relieving topical discomfort and a pressure sensitive adhesive.

The invention also provides a method for alleviating topical discomfort. The method includes applying to the area of the skin inflicted with the topical disorder an adhesive patch of the present invention.

The invention also provides a method for protecting skin inflicted with a topical disorder. The method includes applying an adhesive patch of the present invention to the area of the skin inflicted with the topical disorder.

The invention also provides a method for facilitating the healing process of skin inflicted with a topical disorder. The method includes applying an adhesive patch of the present invention to the area of the skin inflicted with the topical disorder.

DETAILED DESCRIPTION OF THE INVENTION

The adhesive patch of the present invention contains a known, effective and stable amount of antipruritic. The adhesive patch can also comply with FDA regulations. The adhesive patch can effectively cover the entire surface of skin afflicted with a topical disorder. The adhesive patch, therefore, is safe, effective, and convenient for alleviating (i.e., relieving) topical discomfort. The adhesive skin patch 1 can protect the skin inflicted with a topical disorder or the adhesive skin patch 1 can facilitate the healing process of the topical disorder by preventing or diminishing the occurrence of the topical disorder from coming into contact with a contaminant (e.g., clothing, fingernail, hair, grass, an insect, or another person) from the surrounding environment. Such scratching, picking, poking, or otherwise touching the topical disorder could otherwise worsen the topical disorder.

The present invention provides an adhesive patch that contains a medicament. The medicament is present in the therapeutic formulation, which is present on at least a portion of the front side of the backing. The medicament is useful for relieving topical discomfort or for preventing scratching associated with a topical disorder (e.g., insect bite, rash, skin irritation, poison ivy, poison sumac, and poison oak). It has been surprisingly discovered that an adhesive patch can be manufactured wherein the adhesive patch (1) maintains the desired pressure sensitive adhesive properties (2) retains the stability and solubility of the medicament in the therapeutic formulation, (3) can comply with FDA regulations, (4) can effectively cover the entire surface of skin afflicted with a topical disorder, and (5) can alleviate (i.e., relieve) topical discomfort.

Figure 1:
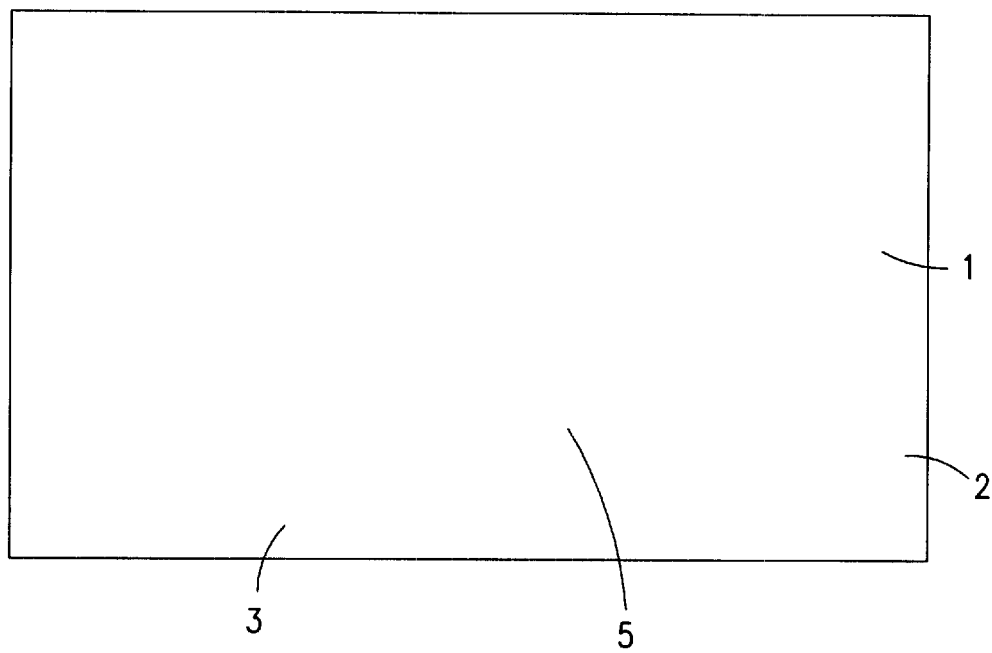
FIG. 1 illustrates the front side of an adhesive patch of the invention.
Figure 2:
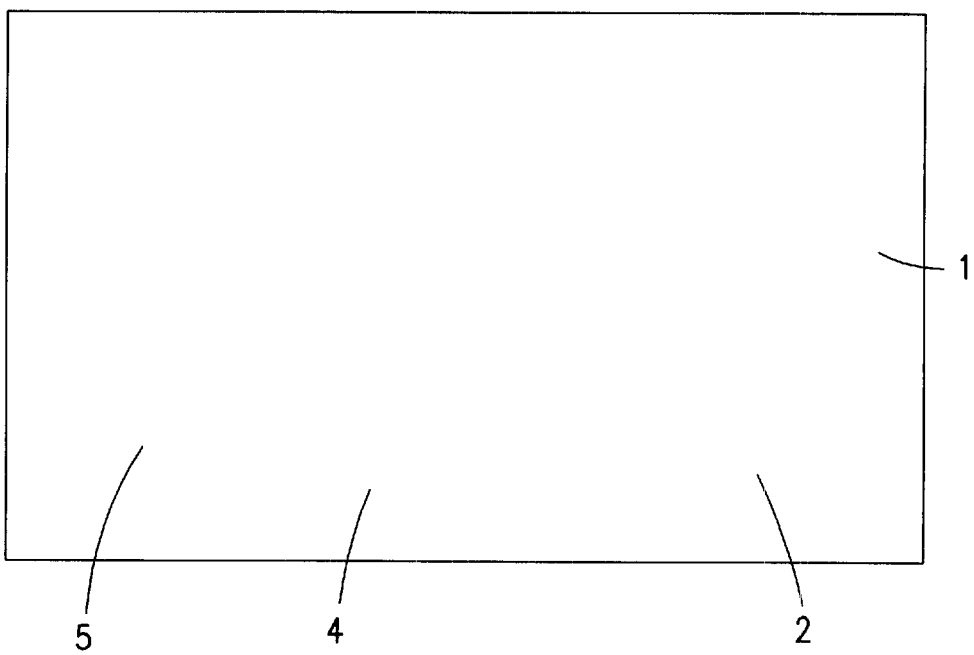
FIG. 2 illustrates the back side of an adhesive patch of the invention.
Figure 3:
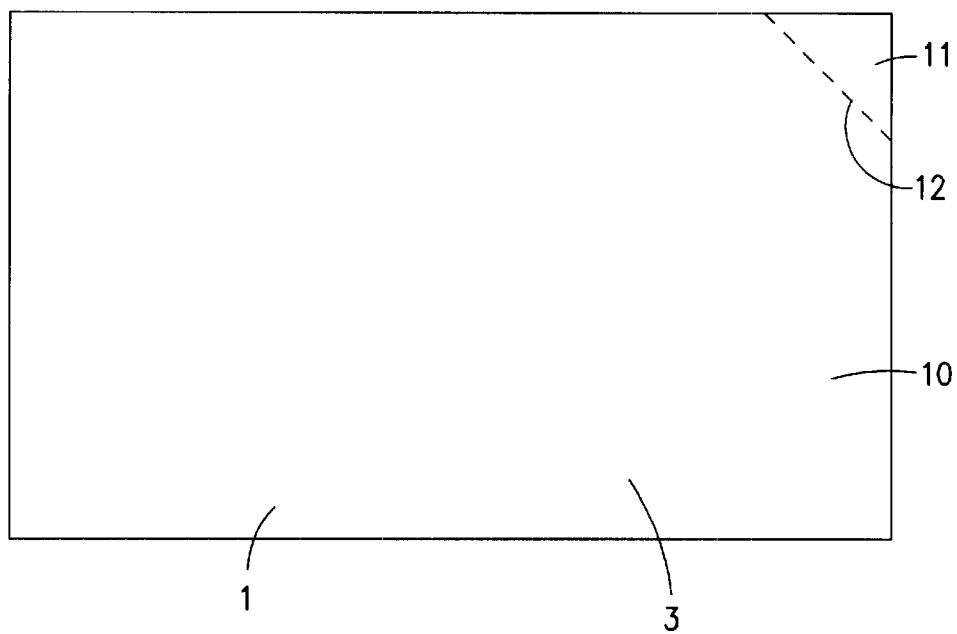
FIG. 3 illustrates the front side of an adhesive patch of the invention with a backing liner attached to the patch.
Figure 4:
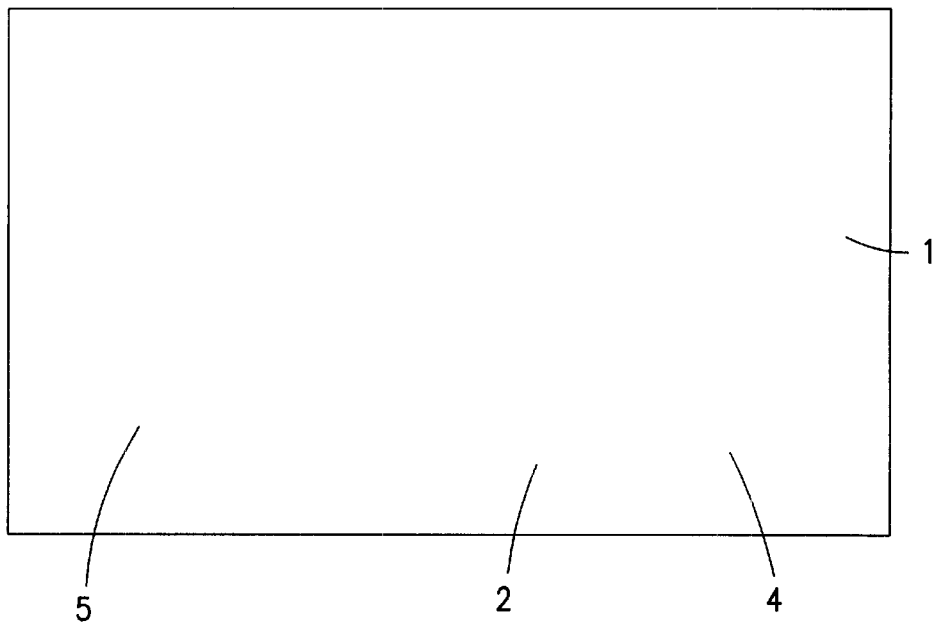
FIG. 4 illustrates the back side of an adhesive patch of the invention with a backing liner attached to the patch.
Figure 5:
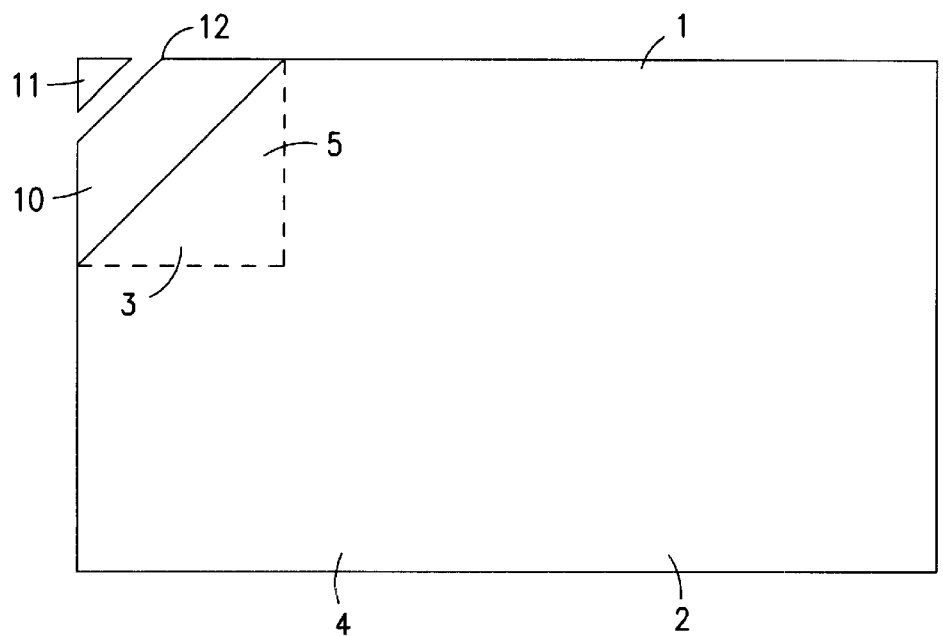
FIG. 5 illustrates the back side of an adhesive patch of the invention with a backing liner attached to the patch, wherein the patch is partially detached from the backing liner.
Figure 6:
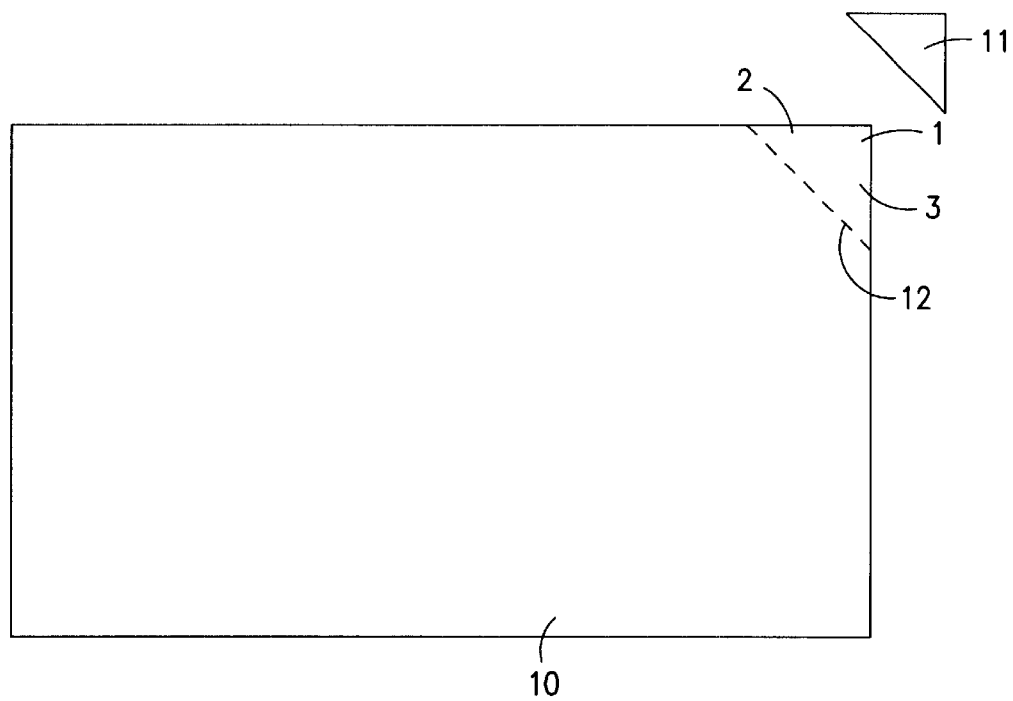
FIG. 6 illustrates the back side of an adhesive patch of the invention with a backing liner attached to the patch, wherein the patch is partially detached from the backing liner.
Figure 7:
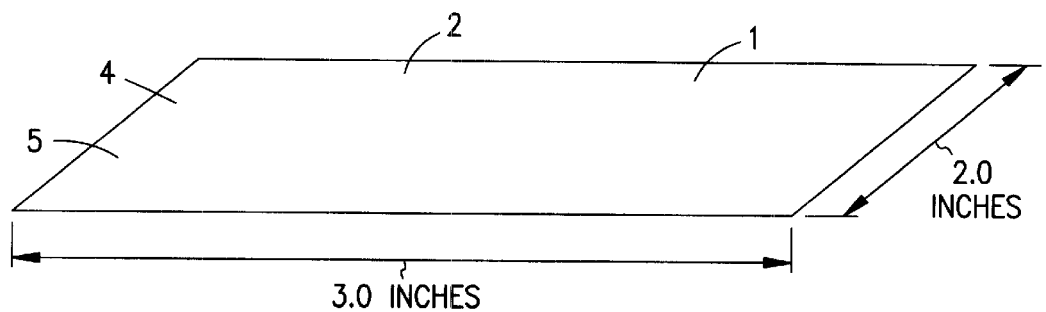
FIG. 7 illustrates a specific adhesive patch of the invention.
Figure 8:
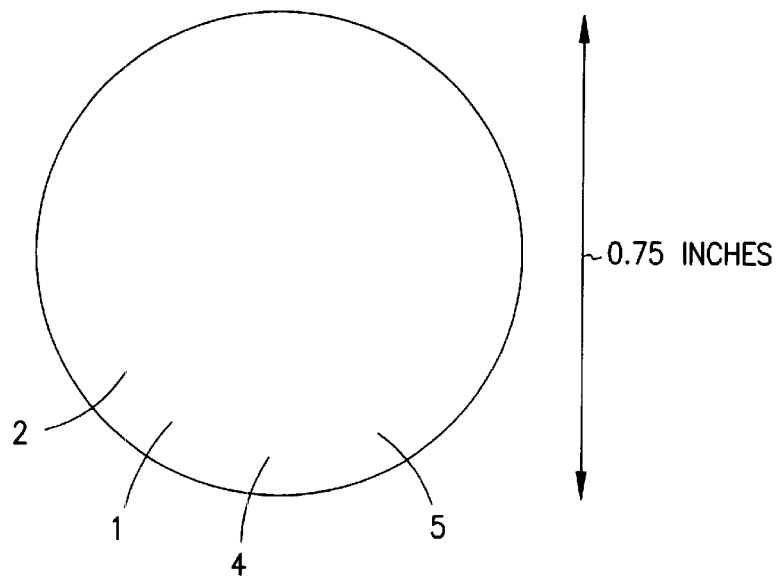
FIG. 8 illustrates a specific adhesive patch of the invention.

Referring to FIGS. 1–8, an adhesive patch 1 of the present invention is provided. The patch 1 includes a backing 2 and a therapeutic formulation 5. The backing 2 is defined by a front side 3 (the side exposed to the skin during use) and a back side 4 (the side exposed to the environment during use). The backing 2 includes a flexible porous sheet of water insoluble material that provides support for the patch 1. The backing 2 should be nonirritating to human skin. The backing is optionally breathable and/or vapor permeable. The backing 2 can be porous since porosity provides openings for receiving the therapeutic formulation 5 and it helps to assure that the patch 1 is vapor permeable. The backing 2 can optionally be woven or non woven. Suitable backings 2 and methods for manufacturing the suitable backings are disclosed in U.S. Pat. Nos. 4,675,009; 5,536,263; 4,696,854; 5,741,510, and references cited therein. The backing 2 can be manufactured from any suitable material, provided the suitable material can form a flexible, bendable, pliable, and/or stretchable sheet of water insoluble porous material.

As shown in FIGS. 1–6, the backing 2 includes a front side 3 and a back side 4. The patch 1 includes a therapeutic formulation 5 located on the front side 3 of the backing 2, wherein the therapeutic formulation 5 includes a combination of a medicament, useful for relieving topical discomfort and a pressure sensitive adhesive. The patch 1 can optionally include a solvent that can effectively dissolve the medicament.

Preferably, the patch 1, upon contact with skin, will allow the skin to breathe. More preferably, the patch 1, upon prolonged contact with skin, will hold in place the therapeutic formulation 5 and allow the skin to breathe over prolonged periods of time, such as up to about 10 days, up to about 1 day, or up to about 8 hours. As such, the adhesive patch 1 of the present invention is preferably vapor permeable and non-occlusive (i.e., breathable).

The backing 2 is a porous, self-supporting sheet of water insoluble, polymeric or natural material that provides strength and integrity for the therapeutic formulation 5. For example, the backing 2 can be water insoluble polymeric fibers, open cell foam backing (e.g., polyurethane, polyvinyl chloride, or polyethylene), a porous film or any other kind of matrix with spaces within the matrix. Preferably, the backing 2 can be polyester, polyurethane, polyolefin, polyamide fibers, natural fibers, cotton fibers, polycellulose fibers, or any mixture thereof.

A specific backing 2 suitable for use in the present invention is a lightweight, porous, pliable strip composed of a nonwoven fabric of polymeric or natural fibers such as polyester, cotton or cellulose fibers. Additional stable, water insoluble flexible sheet materials are disclosed, e.g., in U.S. Pat. Nos. 4,675,009; 5,536,263; 4,696,85; 5,741,510, and references cited therein, and are suitable as backings according to the present invention. The coating of the therapeutic formulation 5 onto, and preferably into, the backing 2 is accomplished with the use of a continuous process mixer, as disclosed in U.S. Pat. No. 5,536,263, and references cited therein.

As shown in FIGS. 3–6, the patch 1 is preferably reversibly attached to a backing liner 10. The backing liner 10 helps to maintain the adhesiveness of the patch 1 prior to use, such as during manufacturing, packaging, shipping, and/or storage. Any suitable backing liner can be employed for use in the present invention. Suitable backing liners 10 are readily known to those of skill in the art. See e.g., U.S. Pat. Nos. 4,675,009; 5,536,263; 4,696,854; 5,741,510, and references cited therein for further descriptions of backing liners useful in the present invention. The backing liner 10 can include a perforation 12 that allows the tab section 11 of the backing liner 10 to be removed (see, FIGS. 5–6). Removal of the tab section 11 of the backing liner 10 allows the patch 1 to be removed from the backing liner 10 with relative ease.

The therapeutic formulation 5 includes a combination of a pressure sensitive adhesive and a medicament useful for relieving topical discomfort. The therapeutic formulation 5 can optionally include a solvent that can effectively dissolve the medicament.

As used herein, "ointment" refers to the substance or substances (e.g., the therapeutic formulation 5) located on a patch. The ointment (e.g., therapeutic formulation) can include a combination of a pressure sensitive adhesive and a medicament useful for relieving topical discomfort. The ointment can optionally include a solvent that can effectively dissolve the medicament.

As used herein, "topical discomfort" is the discomfort associated with an insect bite, rash, skin irritation, poison ivy, poison sumac, or poison oak. As such, the medicament can be an analgesic, an anesthetic, or an antipruritic; as disclosed in Federal Register, Vol. 48, No. 27, §348, and references cited therein. As used herein, an "external analgesic" is a topically (i.e., externally) applied agent that relieves pain by altering perception of nociceptive stimuli without producing anesthesia or loss of consciousness; an "external antipruritic" is a topically (i.e., externally) applied agent that prevents or relieves itching; and an "external anesthetic" is a topically (i.e., externally) applied agent that can reversibly depress neuronal function, producing loss of ability to perceive pain and/or other sensations (see, *Stedman's Medical Dictionary*, 25th Ed., Ill., 1990, p.65, p.77, and p.99).

Preferably, the medicament (e.g., analgesic, anesthetic, or antipruritic) includes one or more of camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate. In one embodiment, the antipruritic can be camphor, menthol or a combination thereof. In another embodiment, the medicament can be lidocaine, hydrocortisone, or a combination thereof. In yet another embodiment, the medicament can be lidocaine, hydrocortisone, camphor, menthol or a combination thereof.

The medicament can be present in any appropriate and suitable amount. Specifically, the medicament can be present in about 0.01 wt. % to about 99.9 wt. % of the therapeutic formulation 5. More specifically, the amount of medicament present in the therapeutic formulation 5 can depend upon the specific compound or compounds employed as the medicament. Preferably, the amount of medicament will comply with Federal Register, Vol. 48, No. 27, §348, and references cited therein.

For example, as disclosed in Federal Register, Vol. 48, No. 27, §348, camphor can be present up to about 3.0 wt. % of the therapeutic formulation and menthol can be present up to about 1.0 wt. % of the therapeutic formulation. In addition, benzocaine can be present in about 5.0 wt. % to about 20.0 wt. % of the therapeutic formulation. Butamben picrate can be present in about 0.5 wt. % to about 1.5 wt. % of the therapeutic formulation. Dibucaine can be present in about 0.25 wt. % to about 1.0 wt. % of the therapeutic formulation. Dibucaine hydrochloride can be present in about 0.25 wt. % to about 1.0 wt. % of the therapeutic formulation. Dimethisoquin hydrochloride can be present in about 0.3 wt. % to about 0.5 wt. % of the therapeutic formulation. Dyclonine hydrochloride can be present in about 0.5 wt. % to about 1.0 wt. % of the therapeutic formulation. Lidocaine can be present in about 0.5 wt. % to about 4.0 wt. % of the therapeutic formulation. Lidocaine hydrochloride can be present in about 0.5 wt. % to about 4.0 wt. % of the therapeutic formulation. Pramoxine hydrochloride can be present in about 0.5 wt. % to about 1.0 wt. % of the therapeutic formulation. Tetracaine can be present in about 1.0 wt. % to about 2.0 wt. % of the therapeutic formulation. Tetracaine hydrochloride can be present in about 1.0 wt. % to about 2.0 wt. % of the therapeutic formulation. Benzyl alcohol can be present in about 10.0 wt. % to about 33.0 wt. % of the therapeutic formulation. Camphor can be present in about 0.1 wt. % to about 3.0 wt. % of the therapeutic formulation. Juniper tar can be present in about 1.0 wt. % to about 5.0 wt. % of the therapeutic formulation. Phenolate sodium can be present in about 0.5 wt. % to about 1.5 wt. % of the therapeutic formulation. Resorcinol can be present in about 0.5 wt. % to about 3.0 wt. % of the therapeutic formulation. Diphenhydramine hydrochloride can be present in about 1.0 wt. % to about 2.0 wt. % of the therapeutic formulation. Tripelennamine hydrochloride can be present in about 0.5 wt. % to about 2.0 wt. % of the therapeutic formulation. Hydrocortisone can be present in about 0.25 wt. % to about 1.0 wt. % of the therapeutic formulation. A corticosteroid can be present in about 0.25 to about 5.0 wt. % of the therapeutic formulation. Camphor can be present in about 3 wt. % to about 10.8 wt. % of the therapeutic formulation with phenol in accordance with Federal Register, Vol. 48, No. 27, §348.20(a)(4). Camphor can be present in about 3 wt. % to about 10.8 wt. % of the therapeutic formulation with metacresol in about 1 wt. % to about 3.6 wt. % of the therapeutic formulation, as caphorated metacresol. In addition, hydrocortisone acetate can be present in about 0.25 wt. % to about 1.0 wt. % of the therapeutic formulation. See, e.g., Federal Register, Vol. 48, No. 27, §348.

The medicament can be located on any portion of the therapeutic formulation on the front side 3 of the backing 2. Preferably, the medicament can be located on and in any portion of the therapeutic formulation on the front side 3 of the backing 2. In addition, the medicament can be located on the entire portion of the therapeutic formulation on the front side 3 of the backing 2. Preferably, the medicament can be located on and in the entire portion of the therapeutic formulation on the front side 3 of the backing 2. When the adhesive skin patch 1 is placed upon the skin of a patient, the medicament can be in continuous contact with the skin of the patient.

The therapeutic formulation 5 can optionally include a solvent that can effectively dissolve the medicament. Any suitable solvent can be employed, provided the solvent effectively dissolves the medicament, the solvent maintains the adhesive properties of the pressure sensitive adhesive, and the solvent maintains the appropriate stability of the medicament during the manufacturing, shipping, and/or storage of the patch 1. Preferably, this maintenance and stability is maintained over a prolonged period of time, e.g., at least about 2 years, at least about 1 year, or at least about 6 months, typically experienced in the manufacturing, shipping, and/or storage of the patch 1. Suitable solvents include water, alcohols (e.g., butanol), polyhydric alcohols (e.g., propylene glycol and polyethylene glycol), one or more fragrances, as described herein below, and combinations thereof.

When the therapeutic formulation 5 includes a solvent, any suitable amount of solvent (e.g., propylene glycol and/or polyethylene glycol) can be employed, provided the amount of solvent employed effectively dissolves the medicament, maintains the adhesive properties of the pressure sensitive adhesive, and maintains the appropriate stability of the medicament during the manufacturing, shipping, and/or storage of the patch 1.

The suitable amount of solvent will typically depend upon the specific solvent employed. For example, propylene glycol can be present up to about 40 wt. % of the therapeutic formulation 5 and polyethylene glycol can be present up to about 25.0 wt. % of the therapeutic formulation. Preferably, propylene glycol can be present in about 6.0 wt. % to about 12.0 wt. % of the therapeutic formulation 5 and polyethylene glycol can be employed in about 0.25 wt. % to about 0.750 wt. % of the therapeutic formulation. More preferably, propylene glycol can be present in about 8.0 wt. % to about 10.0 wt. % of the therapeutic formulation 5 and polyethylene glycol can be employed in about 0.4 wt. % to about 0.6 wt. % of the therapeutic formulation.

In another embodiment of the present invention, the solvent can be a fragrance (i.e., the fragrance can be employed to dissolve the medicament), wherein the fragrance is discussed herein below. In such an embodiment, the fragrance is not an optional component of the therapeutic formulation but is an essential component used to dissolve the medicament.

The pressure sensitive adhesive can include an adhesive, a polymer, and a humectant. The pressure sensitive adhesive can optionally be a gel. Any suitable adhesive can be employed, provided the adhesive employed maintains the adhesive properties (i.e., tackiness) of the pressure sensitive adhesive and maintains the appropriate stability of the medicament during the manufacturing, shipping, and/or storage of the patch 1. Preferably, the adhesive is an acrylic ester copolymer.

Any suitable amount of adhesive can be employed, provided the amount of adhesive employed maintains the adhesive properties of the pressure sensitive adhesive and maintains the appropriate stability of the medicament during the manufacturing, shipping, and/or storage of the patch 1. The suitable amount of adhesive employed can typically depend upon the specific adhesive or adhesives employed. For example, the adhesive can include an acrylic ester copolymer in about 5 wt. % to about 50 wt. % of the therapeutic formulation 5. Preferably, the adhesive can include an acrylic ester copolymer in about 10 wt. % to about 35 wt. % of the therapeutic formulation 5. More preferably, the adhesive can include an acrylic ester copolymer in about 15 wt. % to about 25 wt. % of the therapeutic formulation 5.

Any suitable polymer can be employed, provided the polymer maintains the adhesive properties of the pressure sensitive adhesive and maintains the appropriate stability of the medicament during the manufacturing, shipping, and/or storage of the patch 1. Suitable polymers include starch, starch derivatives, vinyl acetate copolymer, polyvinyl pyrrolidone, polyethylene oxide, algin, derivatives of algin, polyacrylate quats, polymaleic acid, polymaleic anhydride, polyurethanes, polyureas, karaya, gum acacia, locust bean gum, xanthan gum, guar gum, modified guar gum, maltodextrin, carboxymethyl cellulose, carboxypropyl cellulose, polyacrylamide, polyvinyl alcohol, poly AMPS, and polyacrylates. Other suitable polymers are disclosed, e.g., in U.S. Pat. Nos. 4,675,009; 5,536,263; 4,696,854; 5,741,510, and references cited therein. Preferably, the polymer is karaya, which is commercially available from AEP Colloids (Saratoga Springs, N.Y.).

In one embodiment, the polymer can be karaya, polyacrylamide, algin, or a combination thereof. In another embodiment, the polymer can be karaya, algin, or a combination thereof.

Any suitable amount of polymer can be employed, provided the amount of polymer employed maintains the adhesive properties of the pressure sensitive adhesive and maintains the appropriate stability of the medicament during the manufacturing, shipping, and/or storage of the patch 1. Typically, the suitable amount of polymer will typically depend upon the specific polymer employed. For example, karaya can be employed as the polymer in about 10 wt % to about 50 wt. % of the therapeutic formulation 5, in about 15 wt % to about 30 wt. % of the therapeutic formulation 5, or in about 20 wt % to about 30 wt. % of the therapeutic formulation 5.

Any suitable humectant can be employed, provided the humectant maintains the adhesive properties of the pressure sensitive adhesive and maintains the appropriate stability of the medicament during the manufacturing, shipping, and/or storage of the patch 1. As used herein, a humectant is any substance that can be used to provide a moistening effect. Suitable humectants include polyhydric alcohols. One suitable humectant is glycerin, which is commercially available from Dow Chemical (Midland, Mich.). Other suitable humectants include polyhydric alcohols such as ethylene glycol, propylene glycol, triethylene glycol, tetraethylene glycol, and sorbitol.

Any suitable amount of humectant can be employed, provided the amount of humectant employed maintains the adhesive properties of the pressure sensitive adhesive and maintains the appropriate stability of the medicament during the manufacturing, shipping, and/or storage of the patch 1. The suitable amount of humectant can typically depend upon the specific humectant employed. For example, glycerin can be employed as the humectant in about 10 wt % to about 60 wt. % of the therapeutic formulation 5, in about 30 wt % to about 50 wt. % of the therapeutic formulation 5, or in about 35 wt % to about 45 wt. % of the therapeutic formulation 5.

Alternatively, the pressure sensitive adhesive can include a water/lipid emulsion (e.g., water/petroleum), a water based adhesive, hot melt pressure sensitive adhesive or solvent based pressure sensitive adhesive (e.g., polyacrylate, polyisobutylene, and polybutene), rubber, silicone based pressure sensitive adhesives (e.g., polydimethylsiloxane and resin mixtures), polystyrene-polybutadiene-polystyrene, polystyrene-polyisoprene-polystyrene, polystyrene-poly(ethylene-butylene)-polystyrene block polymers, or any combination thereof. In addition, the pressure sensitive adhesive can include a resin emulsion adhesive, wherein the resin emulsion adhesive can include vinyl acetate resin, acrylic ester copolymer, vinyl acetate/diocyl maleate copolymer, acrylic copolymer, or any combination thereof.

Other suitable pressure sensitive adhesives are disclosed, e.g., in U.S. Pat. Nos. 4,675,009; 5,536,263; 4,696,854; 5,741,510, and references cited therein.

The pressure sensitive adhesive can be located on or in any portion of the therapeutic formulation. Preferably, the pressure sensitive adhesive can be located on the entire skin contact side of the therapeutic formulation. When the adhesive skin patch 1 is placed upon the skin surface of a patient, the pressure sensitive adhesive in this configuration is in continuous contact with the skin surface of the patient.

The therapeutic formulation 5 can optionally include a topical moisturizer (i.e., skin conditioner). Any suitable topical moisturizer can be employed, provided the topical moisturizer maintains the adhesive properties of the pressure sensitive adhesive and maintains the appropriate stability of the medicament during the manufacturing, shipping, and/or storage of the patch 1. Suitable topical moisturizers include calamine, aloe, Vitamin E (i.e., tocopheryl), Vitamin E acetate (i.e., tocopheryl acetate), Vitamin C (i.e., L-(+)-ascorbic acid), and lanolin. As used herein, "calamine" is a pink powder of zinc oxide and a skin protectant containing about 98% zinc oxide and about 0.5% ferric oxide; "aloe" is the dried latex of leaves of Curaco Aloe (Aloe barbadenis Miller, Aloe vera Linne) or Cape Aloe (Aloe ferox Miller and hybrids), of the family Liliacaea; "Vitamin E" is 3,4-dihydro-2,5,7,8-tetramethyl-2-(4,8,12-trimethyltridecyl)-2H-1-benzopyran-6-ol; "Vitamin E acetate" is 3,4-dihydro-2,5,7,8-tetramethyl-2-(4,8,12-trimethyltridecyl)-2H-1-benzopyran-6-ol acetate; and "lanolin" is the fat-like secretion of the sebaceous glands of sheep (i.e., complex mixture of esters and polyesters of 33 high molecular weight alcohols and 36 fatty acids) which is deposited onto the wool fibers.

Preferably, the topical moisturizer can be aloe. Aloe is commercially available as Aloe Vera Gel from Terry Laboratories (Melbourne, Fla.). Aloe Vera Gel is commercially available as Aloe Vera Gel 40x(20.0 wt. % solution in water), Aloe Vera Gel 1x(0.5 wt. % solution in water), Aloe Vera Gel 10x(5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

Any suitable amount of topical moisturizer can be employed, provided the amount of topical moisturizer employed maintains the adhesive properties of the pressure sensitive adhesive and maintains the appropriate stability of the medicament during the manufacturing, shipping, and/or storage of the patch 1. The suitable amount of topical moisturizer will typically depend in part upon the specific moisturizer or moisturizers present in the therapeutic formulation 5. For example, the topical moisturizer (e.g., calamine, aloe, Vitamin E (i.e., tocopheryl), Vitamin E acetate (i.e., tocopheryl acetate), Vitamin C (i.e., L-(+)-ascorbic acid), lanolin, or a combination thereof) can be present up to about 40.0 wt. % of the therapeutic formulation 5, up to about 5.0 wt. % of the therapeutic formulation 5, or up to about 1.0 wt. % of the therapeutic formulation 5.

For example, the topical moisturizer can include Aloe Vera Gel, 1xup to about 40.0 wt. % of the therapeutic formulation 5, up to about 5.0 wt. % of the therapeutic formulation 5, or up to about 1.0 wt. % of the therapeutic formulation 5.

The pressure sensitive adhesive includes water. Water can be present in the pressure sensitive adhesive from the adhesive or water can be added to the pressure sensitive adhesive. For example, the adhesive (e.g., acrylic ester copolymer) can typically include water up to about 50 wt. % (i.e., the adhesive is commercially available as an aqueous mixture). In such an embodiment, the water present in the pressure sensitive adhesive can originate solely or in part from the adhesive. Alternatively, water can be added to the pressure sensitive adhesive. For example, the adhesive (e.g., acrylic ester copolymer) will not include any appreciable amount of water and up to about 40 wt. %, 10 wt. %, or 2 wt. % of water (e.g., deionized) can be added to the pressure sensitive adhesive. In addition, water can be present in the pressure sensitive adhesive from the adhesive (e.g., acrylic ester copolymer) and an additional amount of water can be added to the pressure sensitive adhesive.

The therapeutic formulation 5 can optionally include a fragrance or the fragrance can serve as the solvent. Any suitable fragrance can be employed, provided the fragrance maintains the adhesive properties of the pressure sensitive adhesive, maintains the appropriate stability of the medicament during the manufacturing, shipping, and/or storage of the patch 1, and optionally effectively dissolves the medicament. The fragrance preferably is pharmaceutically acceptable for topical use. In addition, it is preferred that the fragrance have a low to moderate volatility, so that its evaporation from the patch 1 is rendered minimal to moderate. The volatility will, however, be high enough such that when desirable, the odor or scent can be detected by the patient. Preferably, the therapeutic formulation 5 of the adhesive patch 1 will emit an odor or scent that is detected by the patient for a period of at least about 10 hours, at least about 8 hours, or at least about 6 hours.

It is appreciated that suitable fragrances are known to those skilled in the art. It is also appreciated that those skilled in the art understand that suitable fragrances are commercially available from, for example, Alpine Aromatics (Piscataway, N.J.), Andrea Aromatics (Princeton, N.J.), Arylessence, Inc. (Marietta, Ga.), Belmay Co., Inc. (Yonkers, N.Y.), Crami Flavor & Fragrance Co., Inc. (City of Commerce, Calif.), Creative Fragrances Mfgr. Inc. (Dallas, Tex.), Drom International Co. (Tawaco, N.J.), Fleurchem, Inc. (Middletown, N.Y.), Great Lakes Chem. Corp. (Lafayette, Ind.), Kraus & Co., Inc. (Battle Creek, Mich.), The Lebermuth Co., Inc. (Mishawaka, Ind.), Penta Manufacturing (Livingston, N.J.), Shaw Mudge & Co. (Shelton, Conn.), Synarome Corp. (NY, N.Y.), Penreco (Houston, Tex.), Tracy Chemical Co. (Portland, Oreg.), Belle-Aire Fragrances (Mundelein, Ill.), Gusta Fragrances Co. (Chesire, Conn.), Atlanta Fragrance (Kennesaw, Ga.), and Bell Flavors & Fragrances, Inc (Northbrook, Ill.).

As the number of suitable fragrances is too voluminous and expansive to exhaustively list herein, suitable fragrances include, e.g., floral scents, fruit scents, plant leaf scents, and any combinations thereof.

Exemplary fragrances include, e.g., grape fragrance, musk fragrance, light vanilla fragrance, Jergens lotion fragrance, Vaseline Intensive Care fragrance, Nivea Lotion fragrance, Ivory Soap fragrance, amaretto, blueberry, coffee, egg nog, peanut butter, rum cake, honey almond, ginger bread house, coffee cake & spice, raspberry rose, sassafras, strawberry, grapefruit pink, home sweet, jeweled citrus, lemon, mango, mulberry, orange flower, Fresh & Clean scent, passion fruit, pikaki, freesia, china rain, coconut, apple, baked bread, cornucopia, lemon chiffon, peppermint twist, white cake, cherry pie, sugar plum, plum, romantic, sea fresh, tea, green floral, honeydew, kiwi, lilac, may bouquet, neutralizer, patchouli, peach, pine apple blossom, chocolate mint, frankincense, baked apple pie, cappuccino, cran-apple, maple syrup, popcorn (buttered), sugar cookie, cotton candy, cranberry cobbler, plumeria, ram, spring fever, watermelon, guava, honeysuckle, hyacinth, macadamia nut, melon, oakmoss, papaya, pear pineapple, blueberry, citrus-ginseng, garden dreams, banana creme pie, chocolate mint, cranberry, macadamia nut, pumpkin pie, chocolate German cake, banana nut bread, sweet potato pie, raspberry, sandalwood, spring flowers, ylang, heather, jasmine, lavender, magnolia, mountain air, orange essence, paradise, peony, alpine breeze, chamomile, clover, gardenia, bubble gum, candy cane, tutti frutti, rose, green apple, cinnamon, cherry, orange sherbet, or any combination thereof.

Any suitable amount of fragrance can be employed in the therapeutic formulation 5, provided the amount of fragrance employed maintains the adhesive properties of the pressure sensitive adhesive, maintains the appropriate stability of the medicament during the manufacturing, shipping, and/or storage of the patch 1, and optionally effectively dissolved the medicament. Typically, the amount of fragrance can typically depend upon the specific fragrance or fragrances employed. For example, when the fragrance is Fresh & Clean fragrance, the fragrance can be employed up to about 5.0 wt. % of the therapeutic formulation 5, up to about 2.0 wt. % of the therapeutic formulation 5, or up to about 0.5 wt. % of the therapeutic formulation 5.

The adhesive skin patch 1 can have any suitable size and shape, provided the adhesive skin patch 1 can effectively cover the topical disorder. Preferably, the adhesive skin patch 1 can effectively cover the entire topical disorder. The adhesive skin patch 1 can be cut, as desired, to provide an adhesive skin patch 1 of a suitable size and shape. The adhesive skin patch 1 can be cut with any suitable cutting device (e.g., scissors, scalpel, or knife).

The adhesive skin patch 1 can be applied to the skin surface of a patient. The adhesive skin patch 1 can be applied to any suitable location on the patient. The adhesive skin patch 1 can be applied to the skin surface of a patient inflicted with a topical discomfort. The skin surface of the patient includes the portion of the skin surface of the patient wherein the entire topical discomfort is located. As such, the patch 1 can be applied to the skin surface of a patient, thereby effectively covering the entire skin surface of the patient inflicted with the topical discomfort.

Since the adhesive skin patch 1 can have any suitable size and shape to effectively cover the topical disorder, the adhesive skin patch 1 can prevent the topical disorder from coming into contact with contaminants (e.g., clothing, fingernail, hair, grass, an insect, etc.) from the surrounding environment. Such contaminants, upon contact with the topical disorder, could increase the scratch stimuli of the patient. The increased scratch stimuli could induce the patient (e.g., child) to scratch, pick, poke, or otherwise touch the topical disorder. The adhesive skin patch 1 can prevent or diminish the occurrence of contaminants from the surrounding environment from coming into contact with the topical disorder. As such, the adhesive skin patch 1 can protect the skin inflicted with a topical disorder or the adhesive skin patch 1 can facilitate the healing process of the topical disorder by preventing or diminishing the occurrence of the topical disorder from coming into contact with a contaminant (e.g., clothing, fingernail, hair, grass, an insect, or another person) from the surrounding environment. In addition, the adhesive skin patch 1 can protect the skin inflicted with a topical disorder or the adhesive skin patch 1 can facilitate the healing process of the topical disorder by preventing or diminishing the occurrence of a patient (e.g., child) from scratching, picking, poking, or otherwise touching the topical disorder. Such scratching, picking, poking, or otherwise touching the topical disorder could otherwise worsen the topical disorder.

The adhesive skin patch 1 can have a rectangular shape. As such, the adhesive skin patch 1 can have a width of about 1.0 inch to about 3.0 inches or about 1.5 inches to about 2.5 inches; a length of about 2.0 inches to about 4.0 inches or about 2.5 inches to about 3.5 inches; and a thickness of about less than about 0.1 inch, less than about 0.01 inch, or less than about 0.001 inch. Preferably, the adhesive skin patch 1 can have a width of about 2.0 inches and a length of about 3.0 inches.

Alternatively, the adhesive skin patch 1 can have a circular shape. As such, the adhesive skin patch 1 can have a diameter of about 0.25 inches to about 5.0 inches or about 0.5 inches to about 1.0 inch. Preferably, the adhesive skin patch 1 can have a diameter of about 0.70 inches to about 0.80 inches.

In one specific embodiment of the present invention, the adhesive skin patch 1 can have a length of about 2.5 inches to about 3.5 inches and a width of about 1.5 inches to about 2.5 inches. See, FIG. 7. In another specific embodiment of the present invention, the adhesive skin patch 1 can have a diameter of about 0.70 inches to about 0.80 inches. See, FIG. 8.

Preferably, the adhesive skin patch 1 can be individually wrapped or multiple adhesive skin patches 1 can be located on, e.g., a card wherein the card is individually wrapped. Some consumers have shown a preference for adhesive skin patches that are individually wrapped. The individually wrapped adhesive skin patch 1 offers to the consumer the ability and convenience of being able to carry a few (e.g., 1, 2, or 3) adhesive skin patches 1 without the extra packaging material.

The therapeutic formulation 5 preferably can remain stable over prolonged period of time, such as from more than about a month to more than about two years. The packaging, shipping, and/or storage of the adhesive skin patch 1 may have an effect upon the duration. The stability of the medicament is due in part to the therapeutic formulation 5 including the medicament in an adhesive formulation. The adhesive formulation is a hydrogel that holds the medicament in an available form while maintaining the necessary stability, pressure sensitive adhesion and effectiveness over prolonged periods of time.

The therapeutic formulation 5 can be positioned on any portion of the front side 3 of the backing 2. Preferably, the therapeutic formulation 5 can be positioned on the entire front side 3 of the backing 2. In this latter configuration, the therapeutic formulation 5 will be in continuous contact with the entire front side 3. When the adhesive skin patch 1 is placed upon the skin surface of a patient, the therapeutic formulation 5 will be in continuous contact with the skin surface of the patient.

Alternatively, a portion of the front side of the backing can contain the therapeutic formulation 5 and other portions of the front side of the backing can contain any combination of the pressure sensitive adhesive, medicament, and solvent. For example, a central circular portion of the front side of the backing can contain the therapeutic formulation 5 and solvent while the remaining ring portion of the front side contains only the pressure sensitive adhesive.

The invention will now be illustrated by the following non-limiting Examples.

EXAMPLES

Example 1: Therapeutic Formulation (in wt. %)

| Component | Weight % |
|---|---|
| Menthol | 1.000 |
| Camphor | 3.000 |
| Propylene Glycol | 8.100 |
| Fragrance | 0.300 |
| Glycerin | 45.400 |
| Calamine | 1.200 |
| Aloe Vera Decolorized 1X | 1.000 |
| Karaya | 22.300 |
| Acrylic Ester Copolymer Adhesive | 17.700 |

Example 2: Therapeutic Formulation (in wt. %)

| Component | Weight % |
|---|---|
| Lidocaine | 4.000 |
| Propylene Glycol | 5.000 |
| Glycerin | 42.600 |
| Aloe Vera Decolorized 1X | 1.000 |
| Polyacrylamide | 17.700 |
| Deionized Water | 5.500 |
| Acrylic Ester Copolymer Adhesive | 24.200 |

Example 3: Therapeutic Formulation (in wt. %)

| Component | Weight % |
|---|---|
| Hydrocortisone | 1.000 |
| Propylene Glycol | 7.100 |
| Polyethylene Glycol | 0.400 |
| Fragrance | 2.500 |
| Glycerin | 43.400 |
| Aloe Vera Decolorized 1X | 0.500 |
| Calamine | 1.000 |
| Polyacrylamide | 23.000 |
| Acrylic Ester Copolymer Adhesive | 21.100 |

Example 4: Therapeutic Formulation (in wt. %)

| Component | Weight % |
|---|---|
| Menthol | 0.700 |
| Camphor | 2.600 |
| Propylene Glycol | 10.300 |
| Fragrance | 5.500 |
| Glycerin | 38.100 |
| Calamine | 1.200 |
| Aloe Vera Decolorized 1X | 0.800 |
| Algin | 18.500 |
| Acrylic Ester Copolymer Adhesive | 23.500 |

Example 5: Therapeutic Formulation (in wt. %)

| Component | Weight % |
|---|---|
| Menthol | 1.000 |
| Camphor | 3.000 |
| Propylene Glycol | 2.300 |
| Fragrance | 4.500 |
| Glycerin | 39.600 |
| Calamine | 1.000 |
| Aloe Vera Decolorized 1X | 0.700 |
| Karaya | 28.300 |
| Deionized Water | 4.600 |
| Acrylic Ester Copolymer Adhesive | 15.000 |

Example 6: Therapeutic Formulation (in wt. %)

| Component | Weight % |
|---|---|
| Menthol | 1.000 |
| Camphor | 3.000 |
| Propylene Glycol | 2.300 |
| Fragrance | 4.500 |
| Glycerin | 39.600 |
| Calamine | 1.000 |
| Aloe Vera Decolorized 1X | 0.700 |
| Karaya | 28.300 |
| Deionized Water | 4.600 |
| Acrylic Ester Copolymer Adhesive | 15.000 |

Example 7: Therapeutic Formulation (in wt. %)

| Component | Weight % |
|---|---|
| Menthol | 1.000 |
| Camphor | 2.000 |
| Propylene Glycol | 6.100 |
| Polyethylene Glycol | 0.400 |
| Fragrance | 1.100 |
| Glycerin | 40.600 |
| Calamine | 1.300 |
| Aloe Vera Decolorized 1X | 0.200 |
| Polyacrylamide | 24.100 |
| Deionized Water | 10.00 |
| Acrylic Ester Copolymer Adhesive | 13.200 |

Example 8: Therapeutic Formulation (in wt. %)

| Component | Weight % |
|---|---|
| Lidocaine | 2.500 |
| Camphor | 3.000 |
| Propylene Glycol | 8.400 |
| Polyethylene Glycol | 0.700 |
| Fragrance | 0.500 |
| Glycerin | 42.400 |
| Aloe Vera Decolorized 1X | 1.000 |
| Algin | 22.500 |
| Deionized Water | 4.000 |
| Acrylic Ester Copolymer Adhesive | 15.000 |

Example 9: Therapeutic Formulation (in wt. %)

| Component | Weight % |
|---|---|
| Menthol | 1.000 |
| Camphor | 2.300 |
| Propylene Glycol | 9.100 |
| Polyethylene Glycol | 0.500 |
| Fragrance | 0.300 |
| Glycerin | 40.300 |
| Calamine | 1.100 |
| Aloe Vera Decolorized 1X | 0.900 |
| Karaya | 26.500 |
| Deionized Water | 1.400 |
| Acrylic Ester Copolymer Adhesive | 16.600 |

Example 10: Therapeutic Formulation (in wt. %)

| Component | Weight % |
|---|---|
| Menthol | 0.500 |
| Camphor | 1.500 |
| Lidocaine | 3.200 |
| Propylene Glycol | 8.600 |
| Polyethylene Glycol | 0.700 |
| Fragrance | 1.200 |
| Glycerin | 40.400 |
| Calamine | 1.100 |
| Aloe Vera Decolorized 1X | 0.900 |
| Polyacrylamide | 18.900 |
| Deionized Water | 5.000 |
| Acrylic Ester Copolymer Adhesive | 18.000 |

Example 11: Therapeutic Formulation (in wt. %)

| Component | Weight % |
|---|---|
| Menthol | 1.000 |
| Lidocaine | 3.500 |
| Propylene Glycol | 2.300 |
| Polyethylene Glycol | 7.000 |
| Fragrance | 3.400 |
| Glycerin | 42.100 |
| Aloe Vera Decolorized 1X | 1.000 |
| Karaya | 24.500 |
| Deionized Water | 2.500 |
| Acrylic Ester Copolymer Adhesive | 13.000 |

Example 12: Therapeutic Formulation (in wt. %)

| Component | Weight % |
|---|---|
| Hydrocortisone | 1.000 |
| Propylene Glycol | 12.300 |
| Polyethylene Glycol | 2.000 |
| Fragrance | 2.300 |
| Glycerin | 44.500 |
| Aloe Vera Decolorized 1X | 0.900 |
| Polyacrylamide | 19.250 |
| Deionized Water | 3.250 |
| Acrylic Ester Copolymer Adhesive | 14.500 |

Example 13: Therapeutic Formulation (in wt. %)

| Component | Weight % |
|---|---|
| Menthol | 1.000 |
| Propylene Glycol | 5.500 |
| Polyethylene Glycol | 1.000 |
| Fragrance | 0.700 |
| Glycerin | 38.500 |
| Calamine | 0.800 |
| Aloe Vera Decolorized 1X | 1.000 |
| Algin | 26.500 |
| Acrylic Ester Copolymer Adhesive | 25.000 |

Example 14: Therapeutic Formulation (in wt. %)

| Component | Weight % |
|---|---|
| Camphor | 3.000 |
| Propylene Glycol | 9.200 |
| Polyethylene Glycol | 0.800 |
| Fragrance | 1.000 |
| Glycerin | 44.000 |
| Calamine | 1.100 |
| Aloe Vera Decolorized 1X | 0.900 |
| Karaya | 25.100 |
| Deionized Water | 1.400 |
| Acrylic Ester Copolymer Adhesive | 13.500 |

Example 15: Therapeutic Formulation (in wt. %)

| Component | Weight % |
|---|---|
| Lidocaine | 4.000 |
| Propylene Glycol | 10.000 |
| Fragrance | 1.200 |
| Glycerin | 42.300 |
| Calamine | 1.000 |
| Aloe Vera Decolorized 1X | 1.000 |
| Polyacrylamide | 17.500 |
| Polyacrylamide | 17.500 |
| Acrylic Ester Copolymer Adhesive | 23.000 |

Example 16: Therapeutic Formulation (in wt. %)

| Component | Weight % |
|---|---|
| Menthol | 1.000 |
| Camphor | 2.500 |
| Propylene Glycol | 5.000 |
| Fragrance | 0.500 |
| Glycerin | 40.000 |
| Calamine | 3.000 |
| Aloe Vera Decolorized 1X | 1.500 |
| Algin | 22.500 |
| Deionized Water | 7.000 |
| Acrylic Ester Copolymer Adhesive | 17.000 |

Example 17: Therapeutic Formulation (in wt. %)

| Component | Weight % |
|---|---|
| Hydrocortisone | 0.500 |
| Polyethylene Glycol | 2.500 |
| Fragrance | 3.600 |
| Glycerin | 38.900 |
| Calamine | 0.500 |
| Aloe Vera Decolorized 1X | 1.500 |
| Karaya | 24.000 |
| Deionized Water | 10.500 |
| Acrylic Ester Copolymer Adhesive | 18.000 |

Example 18: Therapeutic Formulation (in wt. %)

| Component | Weight % |
|---|---|
| Menthol | 1.000 |
| Camphor | 3.000 |
| Propylene Glycol | 7.000 |
| Polyethylene Glycol | 0.200 |
| Fragrance | 0.500 |
| Glycerin | 40.200 |
| Calamine | 0.900 |
| Aloe Vera Decolorized 1X | 0.700 |
| Karaya | 24.200 |
| Deionized Water | 4.000 |
| Acrylic Ester Copolymer Adhesive | 19.000 |

Example 19: Therapeutic Formulation (in wt. %)

| Component | Weight % |
|---|---|
| Lidocaine | 3.000 |
| Camphor | 1.000 |
| Propylene Glycol | 5.200 |
| Polyethylene Glycol | 3.200 |
| Fragrance | 1.000 |
| Glycerin | 41.000 |
| Polyacrylamide | 25.200 |
| Deionized Water | 5.400 |
| Acrylic Ester Copolymer Adhesive | 15.000 |

Example 20: Therapeutic Formulation (in wt. %)

| Component | Weight % |
|---|---|
| Hydrocortisone | 0.500 |
| Propylene Glycol | 2.300 |
| Polyethylene Glycol | 2.500 |
| Fragrance | 0.700 |
| Glycerin | 41.000 |
| Calamine | 1.000 |
| Aloe Vera Decolorized 1X | 0.700 |
| Algin | 25.900 |
| Deionized Water | 4.200 |
| Acrylic Ester Copolymer Adhesive | 13.000 |

Example 21: Production of Therapeutic Formulation and Adhesive Skin Patch

The oil premix was formed by dissolving menthol, camphor, propylene glycol, polyethylene glycol and the fragrance in a container (e.g., tank or vessel). The glycerin premix was formed by mixing glycerin, calamine, and aloe in a separate container. The adhesive premix was formed by mixing water and the adhesives in a separate container. The oil premix, glycerin premix, and adhesive premix were added to a mixer (e.g., continuous processor mixer). Karaya was then added to the mixer and the contents were then mixed. After thorough mixing, the contents were introduced into a coating roll where the contents were introduced into a knife-over-roll coating system. The mixture was then coated to a nonwoven and heat cured porous material (i.e., the backing). The composite was wound into a roll form with the liner located on the opposite side of the mixture (i.e., gel).

The adhesive patch of the present invention can be formulated or manufactured employing the above components. The adhesive patch of the present invention can be formulated or manufactured as described hereinabove or can be formulated or manufactured using any suitable technique known to those skilled in the art. Preferably, the adhesive patch can be formulated or manufactured as described hereinabove or as described in U.S. Pat. Nos. 5,536,263 and 5,741,510, and references cited therein.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An adhesive patch comprising a backing of a flexible sheet of water insoluble porous material, the backing having a front side and a back side and a therapeutic formulation positioned on at least a portion of the front side; wherein the therapeutic formulation comprises:
    camphor present up to about 3.0 wt. % of the therapeutic formulation;
    menthol present up to about 1.0 wt. % of the therapeutic formulation; and
    a pressure sensitive adhesive.

2. The patch of claim 1 wherein the therapeutic formulation is positioned on the entire front side of the backing.

3. The patch of claim 1 wherein the backing comprises a nonwoven fabric.

4. The patch of claim 1 wherein the backing comprises polycellulose fibers, polyester fibers, polyurethane fibers, polyolefin fibers, polyamide fibers, cotton fibers, or any mixture thereof.

5. The patch of claim 1 wherein the backing comprises open cell foam.

6. The patch of claim 5 wherein the open cell foam comprises polyurethane, polyvinyl chloride, polyethylene, or any combination thereof.

7. The patch of claim 1 wherein upon contact with skin, the backing retains the therapeutic formulation and the patch allows moisture from the skin to pass.

8. The patch of claim 1 further comprising a solvent.

9. The patch of claim 1 wherein the solvent is a polyhydric alcohol.

10. The patch of claim 8 wherein the propylene glycol is present up to about 40.0 wt. % of the therapeutic formulation and wherein polyethylene glycol is present up to about 25.0 wt. % of the therapeutic formulation.

11. The patch of claim 1 wherein the pressure sensitive adhesive comprises an adhesive, a polymer, and a humectant.

12. The patch of claim 11 wherein the adhesive comprises a water/lipid emulsion, a hot melt pressure sensitive adhesive, a solvent based pressure sensitive adhesive, a silicone based pressure sensitive adhesive, a resin emulsion adhesive, a water based adhesive, or any combination thereof.

13. The patch of claim 11 wherein the adhesive comprises a water/lipid emulsion, polyacrylate, polyisobutylene, polybutene, rubber, polystyrene-polybutadiene-polystyrene, polystyrene-polyisoprene-polystyrene, polystyrene-poly (ethylene-butylene)-polystyrene block polymers, vinyl acetate resin, acrylic ester copolymer, vinyl acetate/diocyl maleate copolymer, acrylic copolymer, or any combination thereof.

14. The patch of claim 11 the adhesive is an acrylic ester copolymer.

15. The patch of claim 14 wherein the acrylic ester copolymer is present in about 10.0 wt. % to about 25.0 wt. % of the therapeutic formulation.

16. The patch of claim 11 wherein the polymer is vinyl acetate copolymer, polyvinyl pyrrolidone, algin, derivatives of algin, polymaleic anhydride, copolymers of polymaleic anhydride, karaya, xanthan gum, guar gum, polyacrylamide, polyvinyl alcohol, poly AMPS, or polyacrylates.

17. The patch of claim 16, wherein the karaya is present in about 10.0 wt. % to about 50.0 wt. % of the therapeutic formulation.

18. The patch of claim 11 wherein the humectant is glycerin.

19. The patch of claim 18 wherein the glycerin is present in about 10.0 wt. % to about 60.0 wt. % of the therapeutic formulation.

20. The patch of claim 1 wherein the pressure sensitive adhesive is positioned on the entire front side of the backing.

21. The patch of claim 1 wherein the therapeutic formulation further comprises a fragrance.

22. The patch of claim 21 wherein the fragrance is a floral scent, a fruit scent, a plant leaf scent, or any combination thereof.

23. The patch of claim 22 wherein the fragrance is Fresh & Clean scent.

24. The patch of claim 1 wherein the therapeutic formulation further comprises calamine, aloe, lanolin, glycerin, Vitamin E, Vitamin C, Vitamin E acetate, or any combination thereof.

25. The patch of claim 1 that is individually wrapped or wherein multiple patches are located on a card and the card is individually wrapped.

26. The patch of claim 1 that prevents or diminishes the occurrence of a contaminant from the surrounding environment from contacting the surface of skin inflicted with a topical disorder.

27. The patch of claim 1 that can effectively cover the entire surface of skin inflicted with a topical disorder.

28. An adhesive patch comprising a backing of a flexible sheet of water insoluble porous material, the backing having a front side and a back side and a therapeutic formulation positioned on at least a portion of the front side; wherein the therapeutic formulation comprises:
    camphor present up to about 3.0 wt. % of the therapeutic formulation;
    menthol present up to about 1.0 wt. % of the therapeutic formulation; and
    a pressure sensitive adhesive; wherein the adhesive patch can effectively cover the entire surface of skin inflicted with a topical disorder.

29. An adhesive patch comprising a backing of a flexible sheet of water insoluble porous material, the backing having a front side and a back side and an ointment wherein the ointment comprises:

camphor present up to about 3.0 wt. % of the therapeutic formulation;

menthol present up to about 1.0 wt. % of the therapeutic formulation; and a pressure sensitive adhesive.

30. The adhesive patch of claim 29 wherein the pressure sensitive adhesive is a hot melt adhesive, a solvent based adhesive, a petroleum based adhesive, a water based adhesive, or a combination thereof.

31. A method for alleviating topical discomfort comprising:

applying to the area of the skin inflicted with the topical disorder an adhesive patch comprising a backing of a flexible sheet of water insoluble porous material, the backing having a front side and a back side and a therapeutic formulation positioned on the front side of the backing; wherein the therapeutic formulation comprises:

camphor present up to about 3.0 wt. % of the therapeutic formulation, menthol present up to about 1.0 wt. % of the therapeutic formulation; and a pressure sensitive adhesive.

32. The method of claim 31 wherein the adhesive patch can effectively cover the entire skin surface that is inflicted with the topical disorder.

33. The method of claim 32 wherein the topical discomfort is itching.

34. The method of claim 33 wherein the itching is caused by an insect bite, a rash, a skin irritation, poison ivy, poison oak, inflammatory skin condition, poison sumac, or any combination thereof.

35. A method for protecting skin inflicted with a topical disorder or for facilitating the healing process of skin inflicted with a topical disorder comprising:

applying to the area of the skin inflicted with the topical disorder an adhesive patch comprising a backing of a flexible sheet of water insoluble porous material, the backing having a front side and a back side and a therapeutic formulation positioned on at least a portion of the front side; wherein the therapeutic formulation comprises:

camphor present up to about 3.0 wt. % of the therapeutic formulation:

menthol present up to about 1.0 wt. % of the therapeutic formulation; and a pressure sensitive adhesive.

36. The method of claim 35 wherein the non-occlusive adhesive patch can effectively cover the entire skin surface that is inflicted with the topical disorder.

37. The method of claim 36 wherein the topical discomfort is itching.

38. The method of claim 37 wherein the itching is caused by an insect bite, a rash, a skin irritation, poison ivy, poison oak, an inflammatory skin condition, poison sumac, or any combination thereof.

39. The method of claim 35 wherein the skin patch prevents or diminishes the occurrence of a contaminant from the surrounding environment from contacting the surface of the skin inflicted with the topical disorder.

40. The method of claim 39 wherein the contaminant is clothing, a fingernail, hair, or grass.

41. The method of claim 35 wherein the skin patch prevents or diminishes the occurrence of a patient from scratching, picking, poking, or otherwise touching the topical disorder.

42. A method for alleviating topical discomfort comprising:

applying to the entire skin surface inflicted with the topical disorder an adhesive patch comprising a backing of a flexible sheet of water insoluble porous material, the backing having a front side and a back side and a therapeutic formulation positioned on at least a portion of the front side; wherein the therapeutic formulation comprises:

camphor present up to about 3.0 wt. % of the therapeutic formulation;

menthol present up to about 1.0 wt. % of the therapeutic formulation; and a pressure sensitive adhesive.

43. A method for protecting skin inflicted with a topical disorder or for facilitating the healing process of skin inflicted with a topical disorder comprising:

applying to the entire skin surface inflicted with the topical disorder an adhesive patch comprising a backing of a flexible sheet of water insoluble porous material, the backing having a front side and a back side and a therapeutic formulation positioned on at least a portion of the front side; wherein the therapeutic formulation comprises:

camphor present up to about 3.0 wt. % of the therapeutic formulation:

menthol present up to about 1.0 wt. % of the therapeutic formulation; and a pressure sensitive adhesive.

44. A method for alleviating topical discomfort comprising:

applying to the area of the skin inflicted with the topical disorder an adhesive patch comprising a backing of a flexible sheet of water insoluble porous material, the backing having a front side and a back side and an ointment positioned on the front side of the backing; wherein the ointment comprises:

camphor present up to about 3.0 wt. % of the therapeutic formulation;

menthol present up to about 1.0 wt. % of the therapeutic formulation; and a pressure sensitive adhesive.

45. An adhesive patch comprising a backing of a flexible sheet of water insoluble porous material, the backing having a front side and a back side and a therapeutic formulation positioned on at least a portion of the front side; wherein the therapeutic formulation comprises:

camphor present up to about 3.0 wt. % of the therapeutic formulation;

menthol present up to about 1.0 wt. % of the therapeutic formulation;

aloe vera;

calamine;

glycerin;

karaya;

polyethylene glycol;

propylene glycol; and an adhesive.

46. An adhesive patch comprising a backing of a flexible sheet of water insoluble porous material, the backing having a front side and a back side and a therapeutic formulation positioned on at least a portion of the front side; wherein the therapeutic formulation comprises:

a medicament useful for relieving topical discomfort, wherein the medicament is at least one of camphor, menthol, benzocaine, butamben picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate; and a pressure sensitive adhesive;

wherein the camphor is present up to about 3.0 wt. % of the therapeutic formulation and menthol is present up to about 1.0 wt. % of the therapeutic formulation; benzocaine is present in above about 5.0 wt. % to about 20.0 wt. % of the therapeutic formulation; butamben picrate is present in about 0.5 wt. % to about 1.5 wt. % of the therapeutic formulation; dibucaine is present in about 0.25 wt. % to about 1.0 wt. % of the therapeutic formulation; dibucaine hydrochloride is present in about 0.25 wt. % to about 1.0 wt. % of the therapeutic formulation; dimethisoquin hydrochloride is present in about 0.3 wt. % to about 0.5 wt. % of the therapeutic formulation; dyclonine hydrochloride is present in about 0.5 wt. % to about 1.0 wt. % of the therapeutic formulation; lidocaine is present in about 0.5 wt. % to about 4.0 wt. % of the therapeutic formulation; lidocaine hydrochloride is present in about 0.5 wt. % to about 4.0 wt. % of the therapeutic formulation; pramoxine hydrochloride is present in about 0.5 wt. % to about 1.0 wt. % of the therapeutic formulation; tetracaine is present in about 1.0 wt. % to about 2.0 wt. % of the therapeutic formulation; tetracaine hydrochloride is present in about 1.0 wt. % to about 2.0 wt. % of the therapeutic formulation; benzyl alcohol is present in about 10.0 wt. % to about 33.0 wt. % of the therapeutic formulation; camphor is present in about 0.1 wt. % to about 3.0 wt. % of the therapeutic formulation; juniper tar is present in about 1.0 wt. % to about 5.0 wt. % of the therapeutic formulation; phenolate sodium is present in about 0.5 wt. % to about 1.5 wt. % of the therapeutic formulation; resorcinol is present in about 0.5 wt. % to about 3.0 wt. % of the therapeutic formulation; diphenhydramine hydrochloride is present in about 1.0 wt. % to about 2.0 wt. % of the therapeutic formulation; tripelennamine hydrochloride is present in about 0.5 wt. % to about 2.0 wt. % of the therapeutic formulation; hydrocortisone is present in about 0.25 wt. % to less than about 1.0 wt. % of the therapeutic formulation; corticosteroid is present in about 0.25 to about 5.0 wt. % of the therapeutic formulation; camphor is present in about 3 wt. % to about 10.8 wt. % of the therapeutic formulation with phenol; camphor is present in about 3 wt. % to about 10.8 wt. % of the therapeutic formulation with metacresol in about 1 wt. % to about 3.6 wt. % of the therapeutic formulation, as camphorated metacresol; or hydrocortisone acetate is present in about 0.25 wt. % to about 1.0 wt. % of the therapeutic formulation.

\* \* \* \* \*

UNITED STATES PATENT AND TRADEMARK OFFICE
CERTIFICATE OF CORRECTION

PATENT NO. : 6,469,227 B1
DATED : August 22, 2002
INVENTOR(S) : Cooke et al.

It is certified that error appears in the above-identified patent and that said Letters Patent is hereby corrected as shown below:

<u>Title page,</u>
Item [75], Inventors, delete "both of MN" and insert -- Teri Buseman, Minnetonka, all of MN --, therefor.

Signed and Sealed this

Eighteenth Day of May, 2004

JON W. DUDAS
*Acting Director of the United States Patent and Trademark Office*